US008641267B2

(12) United States Patent
Baeuerle et al.

(10) Patent No.: US 8,641,267 B2
(45) Date of Patent: Feb. 4, 2014

(54) FLUIDIC CONDUIT WITH REPEATED DISTURBANCE OF LAMINAR FLOW

(75) Inventors: Martin Baeuerle, Waldbronn (DE); Konstantin Choikhet, Waldbronn (DE)

(73) Assignee: Agilent Technologies, Inc., Santa Clara, CA (US)

( * ) Notice: Subject to any disclaimer, the term of this patent is extended or adjusted under 35 U.S.C. 154(b) by 1372 days.

(21) Appl. No.: 12/102,444

(22) Filed: Apr. 14, 2008

(65) Prior Publication Data

US 2009/0255601 A1    Oct. 15, 2009

(51) Int. Cl.
*B01F 5/06* (2006.01)
(52) U.S. Cl.
USPC .......................................................... 366/338
(58) Field of Classification Search
CPC ............................... B01F 5/061; B01F 5/0647
USPC .......................................................... 366/338
See application file for complete search history.

(56) References Cited

U.S. PATENT DOCUMENTS

| 3,796,657 | A | * | 3/1974 | Pretorius ....................... 210/635 |
| 5,032,283 | A | | 7/1991 | Scott et al. |
| 5,921,678 | A | * | 7/1999 | Desai et al. ................... 366/336 |

OTHER PUBLICATIONS

Dong, Michael; "Ultrahigh-Pressure LC in Pharmaceutical Analysis: Performance and Practical Issues"; Chromatography Online, Jul. 1, 2007 accessed: http://chromatographyonline.findanalytichem.com/lcgc/article/articleDetail.jsp?id=439750.*
(Online), KOT Knitted Open Tubular Reaction Delay and Mixing Coils, www.sequant.com, Apr. 11, 2008, 1 page.
H. Engelhardt/U.D. Neue, Reaction Detector with Three Dimensional Coiled Open Tubes in HPLC, article, Jul. 1982, pp. 403-408, vol. number 15, Vieweg & Sohn Verlagsgesellschaft mbH, Germany.

* cited by examiner

*Primary Examiner* — Yogendra Gupta
*Assistant Examiner* — Alison Hindenlang (57) ABSTRACT

A fluidic device, the fluidic device comprising a planar fluidic conduit for conducting a fluid, wherein the fluidic conduit has a plurality of fluidic disturbance features located along at least a section of the fluidic conduit for disturbing a laminar flow of the fluid along the section.

19 Claims, 4 Drawing Sheets

FLUIDIC CONDUIT WITH REPEATED DISTURBANCE OF LAMINAR FLOW

BACKGROUND ART

The present invention relates to a fluidic device.

In liquid chromatography, a fluidic sample and an eluent (liquid mobile phase) may be pumped through conduits and a column in which separation of sample components takes place. The column may comprise a material which is capable of separating different components of the fluidic analyte. Such a material, so-called beads which may comprise silica gel, may be filled into a column tube which may be connected to other elements (like a control unit, containers including sample and/or buffers) by conduits.

When a fluidic sample is pumped through a cylindrical capillary, the Hagen-Poiseuille effect results in a non-uniform velocity profile along a cross-section of the cylindrical capillary and hence of the fluidic sample. Hagen-Poiseuille's law is a physical law concerning the voluminal laminar stationary flow of a viscous liquid through a cylindrical tube with constant circular cross-section. The said non-uniform velocity distribution over the conduit cross-section may result in longitudinal spreading of the zone containing analytes and thus in an undesired deterioration of the separation performance due to band broadening of different fractions of a separated sample.

Knitted Open Tubular reactors are designed to provide an efficient reagent mixing and/or a reaction delay in liquid chromatographic post-column reactions, while preserving the bandwidth of the separated peaks (see http://www.sequant.com/default.asp?ML=11513).

H. Engelhardt, U. D. Neue, "Reaction Detector with Three Dimensional Coiled Open Tubes in HPLC", 1982 Friedrich Vieweg & Sohn Verlagsgesellschaft mbH, pp. 403-408 discloses a reaction detector with non-segmented flow in open tubes as reaction track. To minimize peak broadening, the open tubes are arranged in a three dimensional coiled structure by knitting.

U.S. Pat. No. 5,032,283 discloses a fluid conduit including a three-dimensional tube having a two-dimensional serpentine opening therethrough and exhibiting low peak dispersion which is applicable as an extra-column connection. The serpentine is a continuously curving path having periodic peaks and valleys of substantially uniform amplitude.

However, dispersion effects may still limit performance of fluidic measurement devices which are to be manufactured with a reasonable effort and in a reasonably small dimension.

DISCLOSURE

It is an object of the invention to provide an efficient fluidic device. The object is solved by the independent claims. Further embodiments are shown by the dependent claims.

According to an exemplary embodiment of the present invention, a fluidic device is provided, the fluidic device comprising a planar (for instance having a basically two-dimensional extension) fluidic conduit for conducting a fluid (such as a liquid and/or a gas, optionally having a solid component), wherein the fluidic conduit has a plurality (that is two or more) of flow disturbance features located along at least a section of the fluidic conduit for disturbing a laminar flow of the fluid along the section (particularly when the fluid is pumped along the section, for instance with a high pressure of at least 600 bar).

According to another exemplary embodiment, a method of manufacturing a fluidic device is provided, the method comprising forming a planar fluidic conduit (for instance by etching a planar substrate) for conducting a fluid, wherein the fluidic conduit has a plurality of fluidic disturbance features located along at least a section of the fluidic conduit for disturbing a laminar flow of the fluid along the section.

The term "planar fluidic conduit" may particularly denote a fluidic conduit for conducting a fluid which is formed two-dimensionally or basically two-dimensionally. Two dimensions which may correspond to a plane of a substrate in which the planar fluidic conduit may be formed as a groove may define a trajectory along which the planar fluidic conduit may extend in a continuous manner so that a fluid can be conducted along a defined path in a two-dimensional space. The third dimension of the planar fluidic conduit may be defined by a depth of a groove in a substrate which may be constant along the planar fluidic conduit, thereby not disturbing the planarity. Thus, the planar fluidic conduit may define a fluid flow trajectory which may be arranged within a plane. In contrast to a planar fluidic conduit, a knitted capillary defines a three-dimensional trajectory such as a helical trajectory. In a planar fluidic conduit, a center of mass of a homogeneous fluid conducted through the fluidic conduit may perform a flow characteristic in accordance with a trajectory which lies within a plane. The fluid conduit may comprise multiple planar segments located in different planes of the planar structure, which segments can be interconnected.

The term "fluidic disturbance feature" or "low disturbance feature" may particularly denote any specific feature which intentionally disturbs a laminar flow of the fluid along the section or destroys the Hagen-Poiseulle's flow velocities distribution in the capillary. Such a fluidic disturbance feature may be formed by a wall shape, defining or delimiting the planar fluidic conduit, which may be specifically shaped or designed to redirect a flowing direction of fluid components to promote fluid mixing within a cross-section thus equilibrating the effective velocities of each fluid segment throughout a cross-section and thereby suppressing dispersion effects. However, a fluidic disturbance feature may also be a member provided separately from a wall as a mechanical obstacle positioned within the fluidic path and forcing the fluid to deviate from its former or its undisturbed flowing profile, thereby contributing to turbulent impacts on the fluid flow.

According to an exemplary embodiment, the conventional shortcoming of a limited resolution of a fluid separation system such as a liquid chromatography system due to dispersion effects caused by an inhomogeneous velocity profile of a fluid flowing along a linear conduit may be efficiently suppressed by intentionally arranging multiple fluid disturbance features along the fluid path, thereby disturbing a laminar flow. This disrupts or disturbs a parabolic flow profile in accordance with Hagen-Poiseuille's law and therefore equilibrates a velocity profile of different components or segments of the fluid. This may efficiently suppress dispersion effects and may therefore allow to increase the efficiency or resolution of a sample separation system such as liquid chromatography system. At the same time, the formation of a planar structure in a substrate together with repeated fluidic disturbance features may allow for a very simple and hence cheap architecture for designing dispersion-suppressing conduits.

Next, further exemplary embodiments of the fluidic device will be explained. However, these embodiments also apply to the method.

The plurality of fluidic disturbance features may be adapted for disrupting a laminar flow of the fluid along the section. In other words, an intentional destruction of a Hagen-Poiseuille flow velocity profile may be performed to thereby—repeatedly—prevent the system from formation of local zones characterized by Hagen-Poiseuille-like flow profile. By this, dispersion will be reduced since the formation of a pronounced velocity profile may be prevented.

While conventional approaches usually intend to keep a disturbation of a fluid flowing along a channel as small as possible, exemplary embodiments take contrary measures by intentionally disturbing the fluid flow multiple times. Particularly, a trajectory defining a fluid flow or a center of gravity thereof may follow a line approaching a mathematical non-differentiable function.

The plurality of fluidic disturbance features may promote a turbulent flow of the fluid along the section. Thus, the shape, size and orientation of the fluidic disturbance features may be selected so that a transfer from a laminar flow to a turbulent flow can occur or fluid velocity components laying in the plane of a conduit cross-section arise. A laminar flow may relate to a scenario in which the fluid is moving smoothly along a path or around an object. A fluid flow may become turbulent when being forced to flow around obstructions such as posts or pillars. Turbulence or turbulent flow may be a flow regime characterized by chaotic, stochastic property changes. This may include low momentum diffusion, high momentum convection, and rapid variation of pressure and velocity in space and/or time. The dimensionless Reynolds number may characterize where the flow conditions lead to laminar flow or turbulent flow. For instance, a flow having a Reynolds number above 4000 may be denoted as a turbulent flow, whereas a flow characterized by a Reynolds number below 2100 may be considered as a laminar flow. In a range between 2100 and 4000, a transitional flow characteristics may be assumed.

The fluidic conduit may be delimited by a boundary surface which is defined by a mathematical function which is not differentiable at least one position. More precisely, such a mathematical function may be a trajectory of a wall of a fluidic conduit delimiting the fluid flow in a plan view. In mathematics, a derivative may be denoted as the velocity of change of a property. A derivative may be denoted as an instantaneous velocity of change and can be calculated at a specific instant rather than as an average over time. The process of finding a derivative may be called differentiation. Even if a mathematical function is continuous at a point, it may not be differentiable there. A function is not differential at a specific position when it is not possible to unambiguously calculate a value of the derivative here. At a position at which a function is not differentiable, the function may have a sharp bend, and at this point the derivative may make a jump. Regarding fluid dynamical properties of such a bend, it may promote a turbulent redirection of a fluid component hitting a wall portion associated with such a non-smooth trajectory position. The plurality of fluidic disturbance features may be formed as wall portions located so that a portion of the fluid hits against this wall portion to thereby promote mixing with another portion of the fluid. This may reduce or cancel out undesired dispersion effects.

Additionally or alternatively, the plurality of fluidic disturbance features may comprise one or more mechanical obstacles, particularly pillars or posts, within a fluid path which force(s) the fluid to flow around the at least one mechanical obstacle. Such obstacles may be connected at a wall defining or delimiting the fluid path which allows for a secure connection of the obstacles at a fixed position. It is also possible that such mechanical obstacles are arranged within the fluidic channel without being fixed to the wall, for instance embedded in a packing material for fluid separation, such as embedded in a matrix of chromatographic beads. In such a scenario, the obstacles may be kept in place by a pressuring force between components of the filling material and walls of the fluidic channel.

The planar fluidic conduit may comprise repeated fluidic disturbance features within the section to provide for a repeated fluidic disturbance along this section. Repeated fluidic disturbance features may be arranged in accordance with a specific sequence, for instance periodically. Thus, an ordered structure of disturbing features may be designed introducing sufficient dispersion prevention and at the same time maintaining a sufficiently high fluid flow velocity.

The fluidic disturbance features may be arranged or located along the section in accordance with a pattern, which may be a one- or two-dimensional pattern, or even a three-dimensional pattern. A one-dimensional pattern may relate to the arrangement of obstacles or specific curvature features of the wall along a straight line, for instance at a constant distance from one another. A two-dimensional arrangement may be for instance the arrangement of obstacles or specific wall features in a direction of the fluid flow and in a direction perpendicular thereof, for instance a matrix-like arrangement of obstacles in rows and columns. A three-dimensional pattern may also involve a direction perpendicular to the planar channel, for instance obstacles located on a top wall and on a bottom wall of the channel, not or not only on side walls thereof.

Such a pattern may be a regular pattern, an irregular pattern, or even a random pattern. Thus, different degrees of symmetry, organization and order may be defined.

The fluidic conduit may be delimited by a boundary surface which has a shape of a meander, a sequence of connected circular segments (particularly half circles), a sequence of connected ellipsoidal segments, a saw tooth, a sinusoidal structure, a sequence of connected triangles, a sequence of connected rectangles, a sharp-edged section, or any other shape or design. By configuring the design, specifically desired fluid flow properties may be adjusted.

The fluidic device may comprise a substrate having a planar surface, the planar fluidic conduit being formed in the planar surface of the substrate. Thus, a groove may be formed in the substrate which then serves as an accommodation chamber for the fluid. Such a configuration may be formed by etching or the like.

A further substrate may be provided having a planar surface as well which may be connected to the planar surface of the substrate to therefore form a lid of the fluidic conduit, thereby providing a closed capillary. The formation of the fluidic device based on two connected substrates may be particularly advantageous when using two substrates made of a metal, forming a groove in one of these substrates, and subsequently connecting the substrates by bonding, gluing or the like. Such a configuration may also be stable under high pressure conditions, such as 1200 bar or more, as may be used in modern liquid chromatography systems.

Fluidic devices according to exemplary embodiments may be particularly suitable for use as fluidic connection pieces for connecting parts of a fluidic instrument such as liquid chromatographic system or the like. For example, columns, fractioners, detectors, the like of a liquid chromatography apparatus may be connected by such planar fluidic conduits. However, such planar fluidic conduits may also form part of an actual fluid separation member such as a chromatographic column.

The substrate may be a multi-layer substrate. In other words, the substrate may be formed of a plurality of layers which may be connected to one another, for instance by lamination. Within any layer of such a multi-layer substrate, a structure for the fluidic application may be formed, such as a conduit, electrode structures, separation channels, frits, valves, heating elements, sensor elements such as temperature sensors, etc.

The substrate may comprise a plurality of layers. For instance, three or five layers may form a structure of the fluidic device which may allow for providing all or a plurality of the required components of the fluidic device within the layered structure. Particularly, the substrate may comprise a top layer, a bottom layer and at least one intermediate layer sandwiched between the top layer and the bottom layer. The at least one intermediate layer may comprise a conduit through which the fluidic sample is to be conducted.

The substrate may have an essentially rectangular cross section. Furthermore, the substrate may have a plate-like shape. Typical dimensions of the substrate are a thickness of 3 mm or less, particularly 1 mm or less, as 0.3 mm or less, or even 0.125 mm (0.005 inch) or less and a dimension of several cm in length and in width.

At least a part of the fluidic channel may serve as a processing element provided in a substrate and filled with a separating material. Such a separating material which may also be denoted as a stationary phase may be any material which allows an adjustable degree of interaction with a sample so as to be capable of separating different components of such a sample. The separating material may be a liquid chromatography column filling material or packing material comprising at least one of the group consisting of polystyrene, zeolite, polyvinylalcohol, polytetrafluorethylene, glass, polymeric powder, silicon dioxide, and silica gel, or any of above with chemically modified (coated, capped etc) surface. However, any packing material can be used which has material properties allowing an analyte passing through this material to be separated into different components, for instance due to different kinds of interactions or affinities between the packing material and fractions of the analyte.

At least a part of the processing element may be filled with a fluid separating material, wherein the fluid separating material may comprise beads having a size in the range of essentially 1 µm to essentially 50 µm. Thus, these beads may be small particles which may be filled inside the separation section of the microfluidic device. The beads may have pores having a size in the range of essentially 0.01 µm to essentially 0.2 µm. The fluidic sample may be passed through the pores, wherein an interaction may occur between the fluidic sample and the pores.

The fluidic device may be adapted as a fluid separation system for separating components of the sample. When a mobile phase including a fluidic sample passes through the fluidic device, for instance with a high pressure, the interaction between a filling of the column and the fluidic sample may allow for separating different components of the sample, as performed in a liquid chromatography device.

However, the fluidic device may also be adapted as a fluid purification system for purifying the fluidic sample. By spatially separating different fractions of the fluidic sample, a multi-component sample may be purified, for instance a protein solution. When a protein solution has been prepared in a biochemical lab, it may still comprise a plurality of components. If, for instance, only a single protein of this multi-component liquid is of interest, the sample may be forced to pass the columns. Due to the different interaction of the different protein fractions with the filling of the column (for instance using a gel electrophoresis device or a liquid chromatography device), the different samples may be distinguished, and one sample or band of material may be selectively isolated as a purified sample.

The fluidic device may be adapted to analyze at least one physical, chemical and/or biological parameter of at least one component of the mobile phase. The term "physical parameter" may particularly denote a size or a temperature of the fluid. The term "chemical parameter" may particularly denote a concentration of a fraction of the analyte, an affinity parameter, or the like. The term "biological parameter" may particularly denote a concentration of a protein, a gene or the like in a biochemical solution, a biological activity of a component, etc.

The fluidic device may be implemented in different technical environments, like a sensor device, a test device, a device for chemical, biological and/or pharmaceutical analysis, a capillary electrophoresis device, a liquid chromatography device, a gas chromatography device, an electronic measurement device, or a mass spectroscopy device. Particularly, the fluidic device may be a High Performance Liquid device (HPLC) device by which different fractions of an analyte may be separated, examined and analyzed.

The processing element may be a chromatographic column for separating components of the fluidic sample. Therefore, exemplary embodiments may be particularly implemented in the context of a liquid chromatography apparatus.

The fluidic device may be adapted to conduct a liquid mobile phase through the processing element and optionally a further processing element. As an alternative to a liquid mobile phase, a gaseous mobile phase or a mobile phase including solid particles may be processed using the fluidic device. Also materials being mixtures of different phases (solid, liquid, gaseous) may be processed using exemplary embodiments.

The fluidic device may be adapted to conduct the mobile phase through the system with a high pressure, particularly of at least 600 bar, more particularly of at least 1200 bar.

The fluidic device may be adapted as a microfluidic device. The term "microfluidic device" may particularly denote a fluidic device as described herein which allows to convey fluid through microchannels having a dimension in the order of magnitude of less than 500 µm, particularly less than 200 µm, more particularly less than 100 µm or less than 50 µm or less.

According to an exemplary embodiment planar conduits may be formed of metal or on the basis of a polyimide film or PEEK (polyether-etherketone) film or similar, in which a channel is formed by patterning technology or the like.

For instance, such channels may be etched in the surface of a substrate. It is possible to provide a stainless steel sheet, having for instance a thickness of 125 µm, etching a channel therein and closing the channel by a further stainless steel sheet which may be free of a channel. The two substrates may be connected by bonding and may then form together a high pressure resistant capillary. Such a planar fluid accommodation member may serve as a fluid connection element and may be flexible when being made of thin metal sheets.

Local disturbances induced within the planar channel may disturb a pronounced velocity profile in accordance with Hagen-Poiseuille's theory, thereby suppressing undesired longitudinal dispersion. Incorporated disturbances of a fluidic path may be formed in a flat structure, wherein the channel may be formed in a single plane. Taking such measures may suppress undesired broadening of bands of a separated fluidic sample.

In an HPLC application, different members may be formed by such a fluidic device in portions in which dispersion suppression may be advantageous, for instance as part of an injector, a thermostat, a heat exchanger, a column connection, a measurement cell, etc. It is possible as well to connect different modules by correspondingly shaped connection pieces thereby substituting conventionally dispersion-critical connection elements. A repetition rate according to which fluidic disturbance features are spatially repeated may be between 0.1 mm and 10 mm, for instance around 1 mm.

BRIEF DESCRIPTION OF DRAWINGS

Other objects and many of the attendant advantages of embodiments of the present invention will be readily appreciated and become better understood by reference to the following more detailed description of embodiments in connection with the accompanied drawings. Features that are substantially or functionally equal or similar will be referred to by the same reference signs.

The illustration in the drawing is schematically.

In the following, referring to FIG. 1, a fluidic device 100 according to an exemplary embodiment will be explained.

The fluidic device 100 is adapted as a system for carrying out liquid chromatography investigations. The fluidic device 100 for separating different components of a fluid or a mobile phase which can be pumped through the apparatus 100 comprises a pre-column 101 for pre-processing (for instance sample preparation or sample enrichment) the fluidic sample and comprises an analytical or main column 120 for post-processing the fluidic sample which has already passed the pre-column 101. In other words, the system 100 is a two-stage fluid separation system. Other embodiments may include only a one-stage fluid separation system having only one column, or a multi-stage fluid separation system having multiple (for instance three, four or more) columns.

Figure 1:
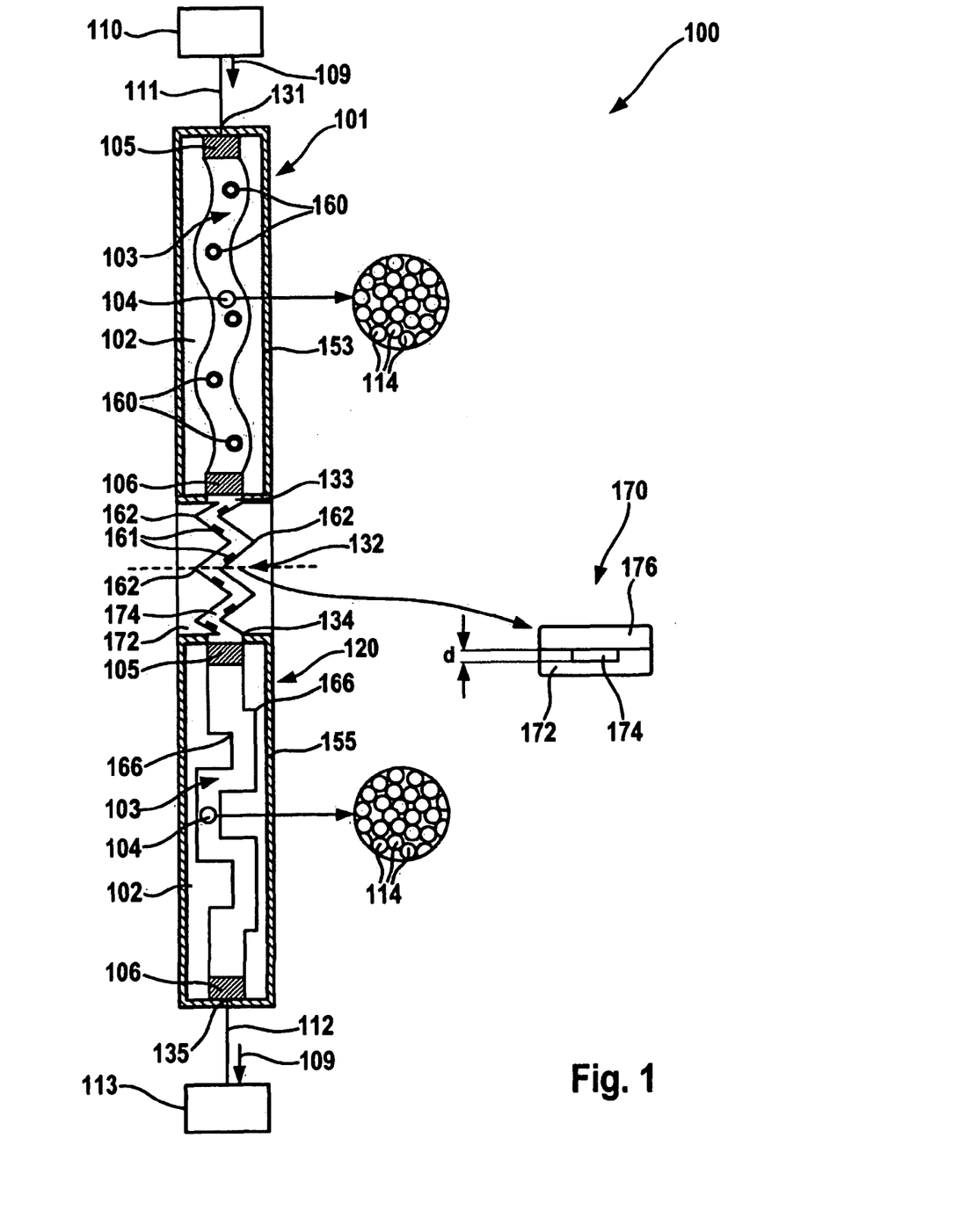
FIG. 1 illustrates a fluidic device according to an exemplary embodiment.

In the embodiment of FIG. 1, each of the fluid separating columns 101, 120 comprises a housing 102 which is shaped to define closed packed channels. Within each of these fluid separating columns 101, 120, a reception 103 is defined which is filled with a package composition 104.

The fluidic device 100 is adapted as a liquid chromatography device 100 and has, in each of the columns 101, 120, a first frit 105 close to an inlet 131, 134 of the respective columns 101, 120, and a second frit 106 provided at an outlet 133, 135 of the respective column 101, 120. The first frit 105 forms the inlet of the respective column 101, 120 and is provided upstream the respective housing 102. The second frit 106 forms the outlet of the respective column 101, 120 and is located downstream of the respective housing 102. A flowing direction of the fluid which is separated using the fluidic device 100 is denoted with the reference numeral 109.

A fluid pump 110 is provided which pumps fluid under pressure of, for instance, 1000 bar through a connection tube 111 and from there to the inlet 131 of the pre-column 101, through the first frit 105 into the housing 102. After having left the column tube 102, that is to say after having passed the second frit 106, an intermediate tube 132 connected to an outlet 133 of the pre-column 101 transports the pre-processed analyte to the inlet 134 of the main column 120. The internal construction of the main column 120 is similar to that of the pre-column 101, but may (or may not) differ from the pre-column 101 with respect to size and fluid separating material 114 filled in the reception 103.

In a further stage, the sample is further separated in the main column 120, and the further separated sample leaves the outlet 135 of the main column 120. After having left the housing 102 of the main column 120, that is to say after having passed the second frit 106 of the main column 120, a second tube or pipe 112 transports the separated analyte to a container and analysis unit 113. The container and analysis unit 113 includes cavities or containers for receiving different components of the fluid, and may also fulfill computational functions related to the analysis of the separated component (s).

The housings 102 comprises the filling 104. In other words, a packing composition 104 comprising a plurality of silica gel beads 114 is inserted into the hollow bore 103 of the column tube 102 of each of the columns 101, 120.

The mobile phase is first conducted through the pre-column 101. By selecting an appropriate ACN concentration in a $H_2O$ environment, a fraction of the fluidic sample may first be trapped at a particular position within the housing 102 of the pre-column 101. This procedure may be denoted as a pre-focusing or pre-separation. Components of the mobile phase which are not trapped in the pre-column 101 are collected in a waste unit (not shown).

Afterwards, the $ACN/H_2O$ concentration ratio within the housing 102 of the pre-column 101 may be selectively modified so as to elute the sample trapped at the beads 114 in the housing 102 of the pre-column 101. Then, the fluidic sample will move through the outlet 133 of the pre-column 101, and will enter the inlet 134 of the main column 120 to be trapped in a portion close to the outlet of the frit 105 of the main column 120.

When the fluid passes through the main column 120, components which differ from a fraction to be separated may simply pass through the column 120 without being trapped and may be collected in a waste (not shown). At the end of this procedure, a band of the fraction of the fluidic sample of interest is trapped at a particular position within the main column 120. By again modifying the concentration ratio $ACN/H_2O$, for instance by gradually modifying the respective contributions of these two components, the trapped sample may be released from the main column 120 and may be conducted to the unit 113, for further processing.

As can be taken from FIG. 1, the fluidic channel 103 within the first separation column 101 is adapted as a planar fluidic conduit (defining a fluid flow trajectory within the paper plane of FIG. 1) for conducting the fluidic sample through the apparatus 100. A delimiting wall of this fluidic channel 103 has a wave-like structure thereby repeatedly redirecting fluid flowing through the fluidic channel 103 into another flowing direction to prevent dispersion. Namely, this curvature mixes different fluid components and intentionally disturbs the laminar fluid flow to introduce turbulences in the fluid flow mixing up different components of the fluid. For example, one portion of the fluid flowing quite close to one of the delimiting walls of the fluidic channel 103 and therefore subject to friction with the wall may be redirected to a more central portion of the fluidic flow path, whereas a fluidic component which has previously been in the center of the fluidic path can be redirected towards the walls. By taking these measures, which result from the geometry of the channel 103, a high accuracy of a separation can be achieved, since resolution limiting dispersion effects can be suppressed.

Additionally to the wave-like wall portion of the fluidic channel 103 in the first column 101, a plurality of pillars 160 are arranged in the fluidic channel 103 according to a repeated pattern. The fluid passing through the channel 103 has to flow around the pillars 160, thereby further promoting mixture of the different components.

The wave-like geometry of the channel 103 as well as the provision of the pillars 160 disrupt a laminar flow of the fluidic sample flowing along the direction 109 through the channel 103 and promote a turbulent flow of the fluidic sample. The pillars 160 arranged essentially at a constant distance from one another provide for a regular pattern of fluidic disturbance features. Also the constant "wavelength" of the wave-like wall of the fluidic channel 103 contributes to a well-defined repeated mixing.

Furthermore, between the outlet frit 106 of the first column 101 and the inlet frit 105 of the second column 120, the fluid passes through a planar connection tube 132 having a planar wall geometry which is zigzag-like, or has a triangular geometry. This structure may also be denoted as a saw tooth geometry. The saw tooth geometry of the connection tube 132 involves boundary surface portions 162 shaped as sharp edges or spikes, thereby providing portions of a mathematical function which is not differentiable at these positions 162. Taking this measure may, in a particularly efficient way, promote the disturbance of the laminar flow. Additionally, posts 164 are arranged along the fluidic path 132, which additionally contribute to the fluid flow disturbance.

In contrast to the pillars 160 having a cylindrical geometry and therefore a circular cross-sectional geometry, a cross-section of the pillars 164 is rectangular, thereby additionally involving sharp edges.

In a similar manner as the fluidic channel 103 of the first column 101, also the fluidic channel 103 of the second column 120 is configured to have fluidic disturbance features by involving sharp edges 166 in a meander-shaped or step-shaped wall delimiting the fluidic channel 103.

As can be taken from a cross-sectional view 170 of FIG. 1, the planar connection tube 132 is formed by a lower substrate 172 having an etching groove 174 covered by an upper planar substrate 176. The substrates 172, 176 are made of metal sheets which are bonded to one another by baking. A depth, d, of the planar channel 174 is constant over the entire zig-zag extension of the etching groove 174.

Also the conduits 111, 112 may be designed in a similar manner as the tube 132.

Figure 2:
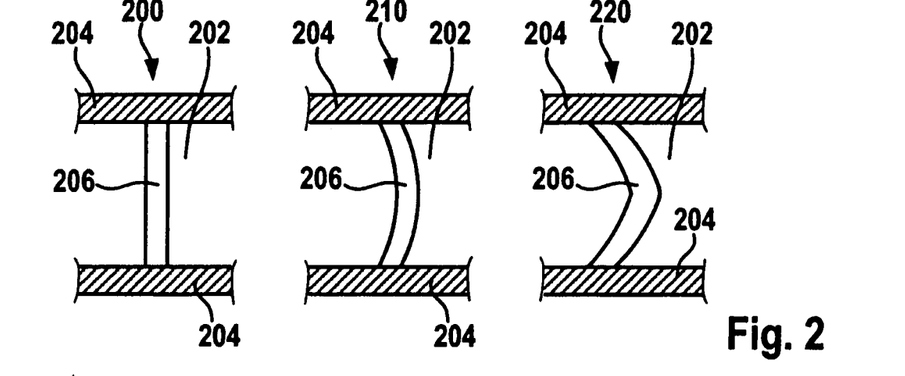
FIG. 2 illustrates dispersion effects in a conventional flow path.

FIG. 2 illustrates how, in conventional systems, a dispersion and therefore a band broadening may occur in an undisturbed fluidic path.

A first image 200 shown in FIG. 2 shows a straight fluidic channel 202 delimited by walls 204. FIG. 2 shows a sample 206 directly after injection into the system.

As can be taken from an image 210 shown in FIG. 2, due to friction at the walls 204, a velocity profile of the fluidic sample 206 is generated, which, as can be taken from a third image 210, with the time increasingly stretches (which is dispersed longitudinally) the sample band. In other words, the Hagen-Poiseuille effect resulting from friction of the moving fluid at the walls 204 results in a for instance parabolic or parabolic-like velocity profile, as shown in image 220.

Figure 3:
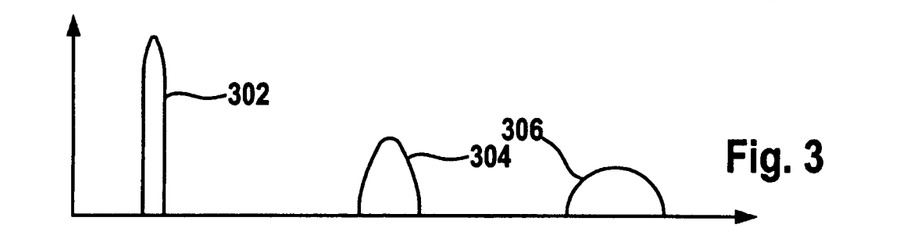
FIG. 3 illustrates peak broadening resulting from the velocity profiles of FIG. 2.

FIG. 3 shows a diagram 300 illustrating schematically a shape of a detection signal indicative of the sample 206 in the three images 200, 210, 220 of FIG. 2.

A first very narrow detection pulse or peak 302 can be detected in the scenario of the image 200. A slightly broadened pulse 304 can be detected at a position corresponding to the image 210 of FIG. 2. A very broad pulse 306 relates to the situation of image 220.

By repeatedly intermixing different portions of the sample 206 within conduit cross-section, exemplary embodiments overcome the problem shown in FIG. 2 and FIG. 3 by repeatedly equilibrating the sample component distribution over cross-section and thus equalizing the mean longitudinal propagation velocities of each and every segment of the sample and fluid in general, thereby ensuring narrow detection peaks which increases efficiency.

Figure 4:
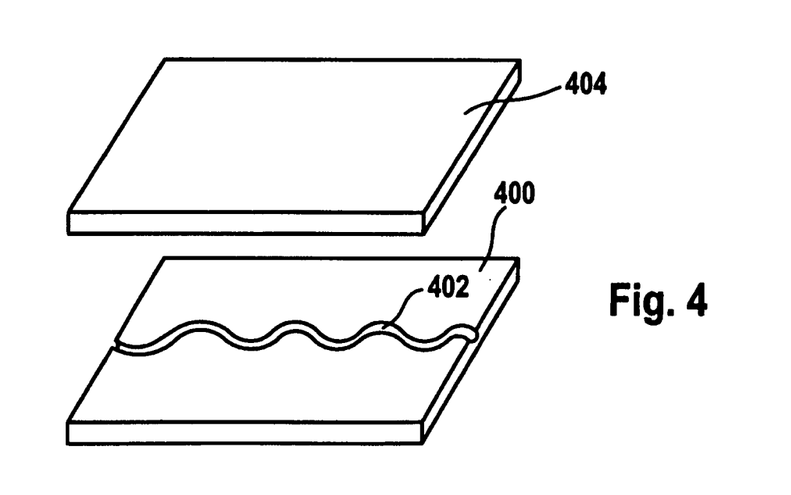
FIG. 4 illustrates two substrates to be connected to one another for forming a fluidic device according to an exemplary embodiment.

FIG. 4 shows a first substrate 400 made of a stainless steel sheet having a thickness of, for instance, 125 µm. A wave-like groove 402 is formed as a fluidic channel by removing a surface portion of the stainless steel substrate 400 by etching. A planar second substrate 404 (also a stainless steel sheet having a thickness of, for instance 125 µm) can be connected to the first substrate 400, for instance by bonding substrates 400, 404 and thereby connecting them permanently, so that a planar surface portion of the second substrate 404 and the groove 402 in the first substrate 400 together form a fluidic conduit according to an exemplary embodiment.

Figure 5:
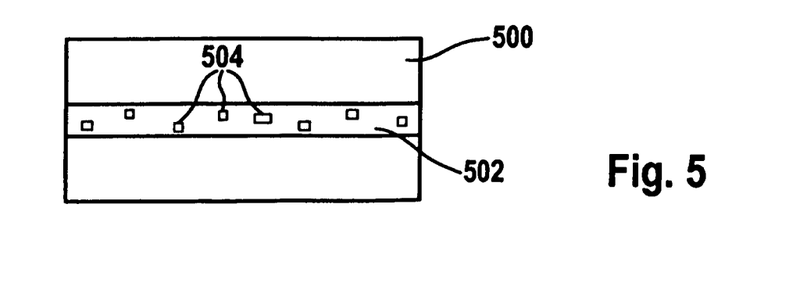
FIG. 5 illustrates a plan view of a grooved substrate as a fluidic device according to an exemplary embodiment.

FIG. 5 shows a plan view of a planar substrate 500 in which an essentially two-dimensional channel 502 has been etched. By providing a repeated pattern of in this embodiment randomly oriented posts 504, fluid disturbance features may be implemented.

Figures 6, 7:
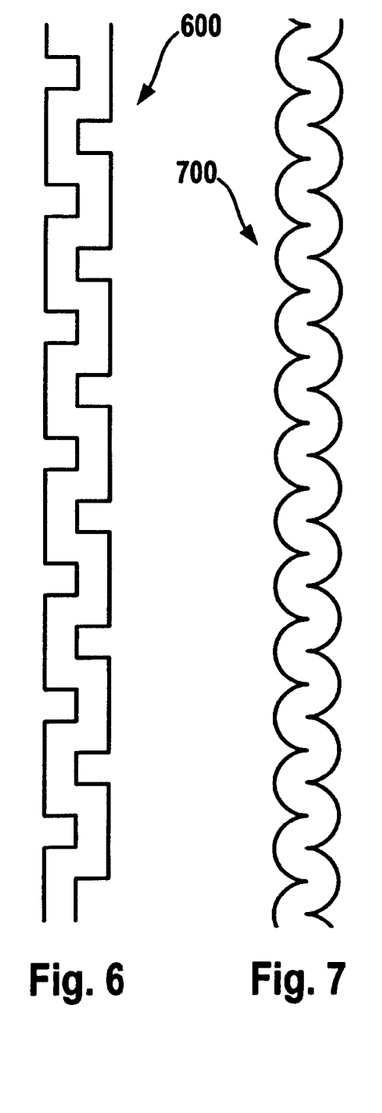
FIG. 6 to FIG. 9 show different geometries of fluidic conduits of fluidic devices according to exemplary embodiments.

FIG. 6 shows a channel geometry 600 having an essentially meander-shaped geometry.

FIG. 7 shows a channel geometry 700 being formed by two sequences of half circles which are laterally displaced relative to one another by one circle radius.

Figure 8:
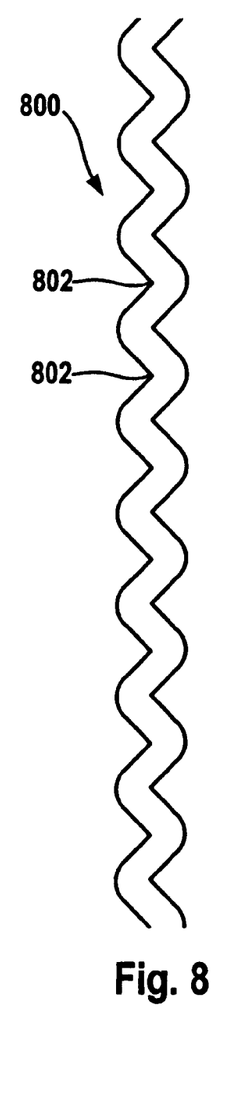

FIG. 8 illustrates a fluidic channel 800 being formed by parts of a sinusoidal curve which are connected to one another to form sharp etches 802.

Figure 9:
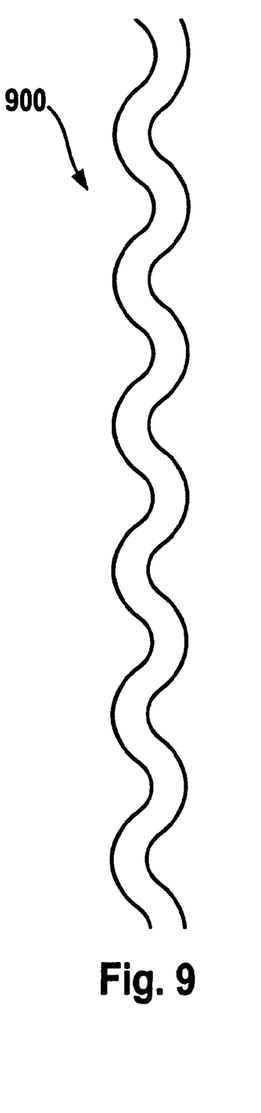

FIG. 9 shows a wave-like geometry of a fluidic channel according to another exemplary embodiment.

Figure 10:
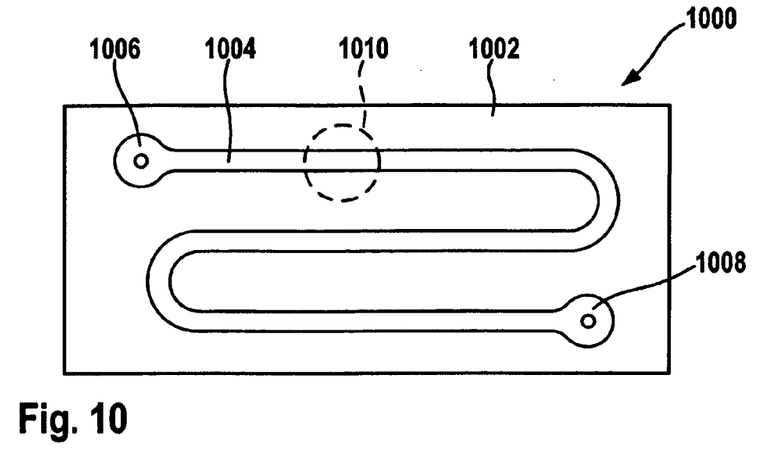
FIG. 10 shows a plan view of a fluidic device according to an exemplary embodiment.

FIG. 10 illustrates a fluidic device 1000 according to another exemplary embodiment.

In FIG. 10, a metal sheet 1002 is provided as a substrate in which a bent channel 1004 is etched. A fluid inlet portion is denoted with reference numeral 1006, and a fluid outlet port is denoted with reference numeral 1008. The fluid inlet port 1006 is separated from and connected to the fluid outlet 1008 by the fluidic channel 1004.

Figure 11:
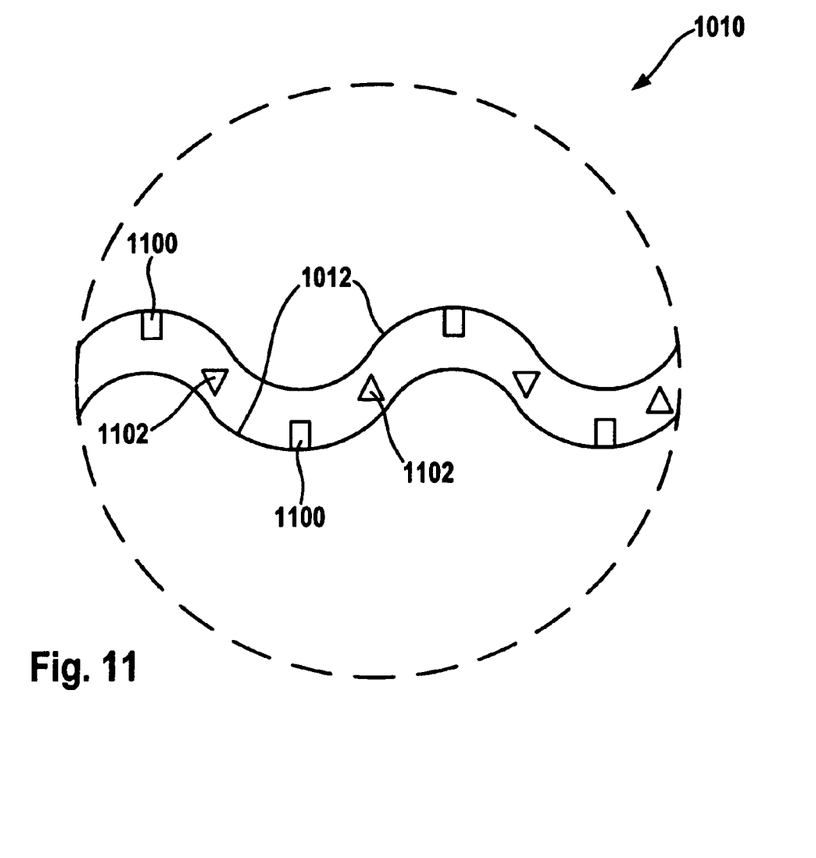
FIG. 11 shows an enlarged view of a part of the fluidic device of FIG. 10.

A portion 1010 of the fluidic channel is illustrated in FIG. 11 in more detail. As can be taken from FIG. 11, the fluidic channel 1004 is delimited by wave-like walls 1012, in which a sequence of first posts 1100 having a rectangular cross-section and being connected to the walls 1012 and second posts 1102 having a triangular cross-section and being independent of the walls 1012 are included. Thus, an efficient continued mixing of the sample flowing through the fluidic channel 1004 may be enabled.

It should be noted that the term "comprising" does not exclude other elements or features and the "a" or "an" does not exclude a plurality. Also elements described in association with different embodiments may be combined. It should also be noted that reference signs in the claims shall not be construed as limiting the scope of the claims.

The invention claimed is:

1. A fluidic device, the fluidic device comprising a planar fluidic conduit for conducting a fluid, wherein the planar fluidic conduit comprises a groove on a substrate and has a plurality of fluidic disturbance features in a repeated pattern located along a length of the fluidic conduit for disturbing a flow velocity distribution being characteristic for laminar flow of the fluid along the section, the fluidic disturbance features constructed and positioned to create fluid velocity components across a cross sectional plane of the fluidic conduit while limiting dispersion effects of a fluid separation in a flow direction.

2. The fluidic device according to claim 1, wherein the plurality of fluidic disturbance features is adapted for disrupting a laminar flow of the fluid along the length of the fluidic conduit.

3. The fluidic device according to claim 1, wherein the plurality of fluidic disturbance features is adapted for disturbing laminar flow or a parabolic-like flow velocity field along the section.

4. The fluidic device according to claim 1, wherein the plurality of fluidic disturbance features is adapted for promoting a turbulent flow of the fluid along the length of the fluidic conduit.

5. The fluidic device according to claim 1, wherein the fluidic conduit is delimited by a boundary surface which is defined by a curve which is not smooth or has sharp edges at least one position.

6. The fluidic device according to claim 1, wherein the plurality of fluidic disturbance features is arranged as a wall portion of the fluidic conduit located so that at least a portion of the fluid is directed against this wall portion to thereby promote mixing of the fluid within a given conduit cross-section.

7. The fluidic device according to claim 1, wherein the fluidic disturbance features comprise at least one mechanical obstacle within a fluid path which at least one mechanical obstacle is arranged to force the fluid to flow around the at least one mechanical obstacle.

8. The fluidic device according to claim 1,
wherein the planar fluidic conduit comprises repeated fluidic disturbance features within the section to provide for a repeated fluidic disturbance or a repeated laminar flow disruption of the fluid along the section.

9. The fluidic device according to claim 1, comprising at least one of the following features:
the planar fluidic conduit comprises a pattern of fluidic disturbance features along the section; the planar fluidic conduit comprises a regular pattern of fluidic disturbance features along the length of the fluidic conduit;
the planar fluidic conduit comprises an irregular pattern of fluidic disturbance features along the length of the fluidic conduit;
the planar fluidic conduit comprises a random pattern of fluidic disturbance features along the length of the fluidic conduit;
the planar fluidic conduit comprises one of a one-dimensional, a two-dimensional, and a three-dimensional pattern of fluidic disturbance features along the length of the fluidic conduit.

10. The fluidic device according to claim 1,
wherein the fluidic conduit is delimited by a boundary surface which has a shape which comprises at least one of the group consisting of a meander, a sequence of connected circular segments, a sequence of connected ellipsoidal segments, a saw tooth, a sinusoidal structure, a sequence of connected triangles, a sequence of connected rectangles, and a sharp-edged section.

11. The fluidic device according to claim 1,
comprising a substrate having a planar surface, the planar fluidic conduit being formed in the planar surface of the substrate.

12. The fluidic device according to claim 11, comprising at least one of the following features:
at least the section of the planar fluidic conduit has a constant depth in a direction perpendicular to the planar surface of the substrate;
the planar fluidic conduit is etched in the planar surface of the substrate;
the fluidic device comprises a further substrate having a planar surface connected to the planar surface of the substrate to form a lid of the fluidic conduit, thereby providing a closed capillary as the planar fluidic conduit;
the substrate is a multi-layer substrate which comprises a plurality of layers which are connected to one another by lamination;
the substrate comprises a top layer, a bottom layer, and at least one intermediate layer sandwiched between the top layer and the bottom layer;
the substrate comprises a top layer, a bottom layer, and at least one intermediate layer sandwiched between the top layer and the bottom layer, wherein at least one of the at least one intermediate layer comprises the fluidic conduit through which the fluid is to be conducted;
the substrate comprises at least one material of the group consisting of a plastic, a polymer, a metal, a semiconductor, and a ceramic;
the substrate has an essentially rectangular cross section;
the substrate has a plate shape.

13. The fluidic device according to claim 1, comprising at least one of the following features:
the planar fluidic conduit extends exclusively within a two-dimensional plane;
the planar fluidic conduit forms part of at least one of the group consisting of a fluidic connection piece for coupling different modules of a life science apparatus, a fluidic connection piece for coupling different modules of a liquid chromatography apparatus, an injector for a liquid chromatography apparatus, a separation column for a liquid chromatography apparatus, a sample supply conduit for a liquid chromatography apparatus, a heat-exchanger or thereto stating module for a liquid chromatography apparatus, a detector inlet conduit for a liquid chromatography apparatus, and a drain conduit for a liquid chromatography apparatus;
the fluidic device is adapted as a fluidic chip device;
the fluidic device is adapted as a fluid separation system for separating compounds of the fluid;
the fluidic device is adapted as a fluid purification system for purifying the fluid;
the fluidic device is adapted to analyze at least one physical, chemical and/or biological parameter of at least one compound of the fluid;
the fluidic device comprises at least one of the group consisting of a sensor device, a test device for testing a device under test or a substance, a device for chemical, biological and/or pharmaceutical analysis, a capillary electrophoresis device, a liquid chromatography device, an HPLC device, a gas chromatography device, a gel electrophoresis device, an electronic measurement device, and a mass spectroscopy device;
the fluidic device is adapted to conduct the fluid with a high pressure;
the fluidic device is adapted to conduct the fluid with a pressure of at least 100 bar;
the fluidic device is adapted to conduct a liquid fluid;
the fluidic device is adapted as a microfluidic device;
the fluidic device is adapted as a nanofluidic device.

14. The fluidic device according to claim 1, comprising a processing element provided in the section of the fluidic conduit and adapted for interacting with the fluid.

15. The fluidic device according to claim 14, comprising at least one of the following features:
- the processing element is adapted for retaining a part of sample components and for allowing other components of the mobile phase to pass the processing element;
- the processing element comprises a separation column;
- the processing element comprises a chromatographic column for separating components of a fluidic sample;
- at least a part of the processing element is filled with a fluid separating material;
- at least a part of the processing element is filled with a fluid separating material, wherein the fluid separating material comprises beads having a size in the range of 1 µm to 50 µm;
- at least a part of the processing element is filled with a fluid separating material, wherein the fluid separating material comprises beads having pores having a size in the range of 0.01 µm to 0.2 µm.

16. The fluidic device according to claim 1, wherein the fluidic conduit is delimited by a boundary surface which is defined by a curve which is not smooth or has sharp edges at a plurality of periodically repeating positions.

17. The fluidic device according to claim 1, wherein the fluidic disturbance features comprise at least one pillar within a fluid path, wherein the at least one pillar is arranged to force the fluid to flow around the at least one pillar.

18. The fluidic device according to claim 1, wherein the fluidic device is adapted to conduct the fluid with a pressure of at least 500 bar.

19. The fluidic device according to claim 1, wherein the fluidic device is adapted to conduct the fluid with a pressure of at least 1000 bar.

* * * * *